United States Patent [19]

Iwasaki

[11] 4,019,376
[45] Apr. 26, 1977

[54] HARDNESS TESTER

[75] Inventor: Shozo Iwasaki, Ebina, Japan

[73] Assignee: Kabushiki Kaisha Akashi Seisakusho, Japan

[22] Filed: Sept. 4, 1975

[21] Appl. No.: 610,398

[30] Foreign Application Priority Data

Sept. 11, 1974 Japan .......................... 49-104672

[52] U.S. Cl. .................................................. 73/81
[51] Int. Cl.[2] ........................................ G01N 3/48
[58] Field of Search .......................... 73/81, 85, 83

[56] References Cited

UNITED STATES PATENTS

| | | | |
|---|---|---|---|
| 1,661,718 | 3/1928 | Davis | 73/81 |
| 2,520,387 | 8/1950 | Dobry et al. | 73/81 |
| 2,536,632 | 1/1951 | Ernst | 73/81 |
| 3,077,771 | 2/1963 | Ernst | 73/81 |
| 3,934,463 | 1/1976 | Venderjagt | 73/81 |

FOREIGN PATENTS OR APPLICATIONS 845,423  6/1952  Germany ............................ 73/81

Primary Examiner—James J. Gill
Assistant Examiner—Anthony V. Ciarlante
Attorney, Agent, or Firm—Robert E. Burns; Emmanuel J. Lobato; Bruce L. Adams

[57] ABSTRACT

A hardness tester for measuring hardness of a material by pressing an indenter attached to the lower end of a load application shaft into the test specimen. A reference cylinder is coaxially and slidably fitted around the load application shaft, and a datum plane, to be in contact with the specimen, is formed at the lower end of the reference cylinder, so as to limit the penetration depth of the indenter into the specimen to a predetermined constant depth. A stop device is provided for regulating the descending of the load application shaft relative to the reference cylinder. A load detector for hardness measurement is interposed on the load application shaft, to measure the hardness of the specimen by measuring the force applied to produce an indentation of a predetermined size on it.

5 Claims, 9 Drawing Figures

HARDNESS TESTER

BACKGROUND OF THE INVENTION

The present invention relates to a hardness tester that measures hardness of a material by pressing an indenter attached to the lower end of a load application shaft into the test specimen.

With the conventional hardness testers of this type, a predetermined test load has been applied to produce an indentation of variable dimensions in the surface of the specimen. Then, the area or the depth of the indentation was measured to determine the hardness of the material being tested. A high degree of technical skill was needed to accomplish accurate measurement of the area or depth of such indentation.

SUMMARY OF THE INVENTION

This invention has been made to solve the problem that has been encountered with the conventional hardness testers. The primary object of this invention is to provide a hardness tester which determines the hardness of a material by measuring a variable force, applied to produce an indentation of a predetermined size on it. The force required to produce an indentation of a predetermined size differs with the hardness of materials.

In order to achieve the primary object, a hardness tester according to this invention comprises a load application shaft coaxially and slidably fitted in a reference cylinder, said load application shaft being fitted with an indenter at the lower end thereof and a load detector, to determine hardness, at an upper position thereof. A datum plane is provided at the lower end of said reference cylinder so as to be in contact with the specimen, and a stopper meachanism is provided above said load detector, to limit the depth of descent of the load application shaft relative to the reference cylinder.

In the above-described hardness tester of this invention, after bringing the datum plane at the lower end of the reference cylinder in contact with the specimen, the load application shaft is lowered along the reference cylinder until it is stopped by the stopper mechanism. Thereby, the indenter at the lower end of the load application shaft is pressed into the specimen to a predetermined extent. The load required for the performance of this impression is measured by the load detector. Hardness of the material being tested is determined from the reading of the load detector. Preferably, a maximum value detector detects the maximum load. By these expedients, determination of hardness can be effected with greater ease and speed than before.

Further, one embodiment of the hardness tester according to this invention has the following feature. A guide cylinder to guide the axial movement of the reference cylinder is provided, the reference cylinder being snugly fitted therein so that it can be moved up and down by means of a spring control. Outside this guide cylinder is provided a press cylinder that is capable of sliding coaxially therewith by means of another spring. A prior pivot to transmit the pressing load is provided between a press member fixed at the top of the press cylinder and the upper end of said load application shaft.

In the hardness tester thus equipped, the reference cylinder is guided by the guide cylinder while it is descending toward the specimen until the datum plane at the bottom thereof comes in contact with the surface of the specimen. This facilitates pushing the load application shaft through the reference cylinder at right angles with the surface of the specimen. Also, the transmission of the pressing load by way of the pivot between the press member and the load application shaft prevents rotation torque from being transmitted to the load application shaft. This permits accurate pressing of the indenter into the specimen, resulting in highly precise determination of hardness.

BRIEF DESCRIPTION OF THE DRAWINGS

In order that this invention may be fully understood, preferred embodiments thereof will now be described by way of example, by reference to the accompanying drawings, in which.

DESCRIPTION OF THE PREFERRED EMBODIMENTS

Figure 1:
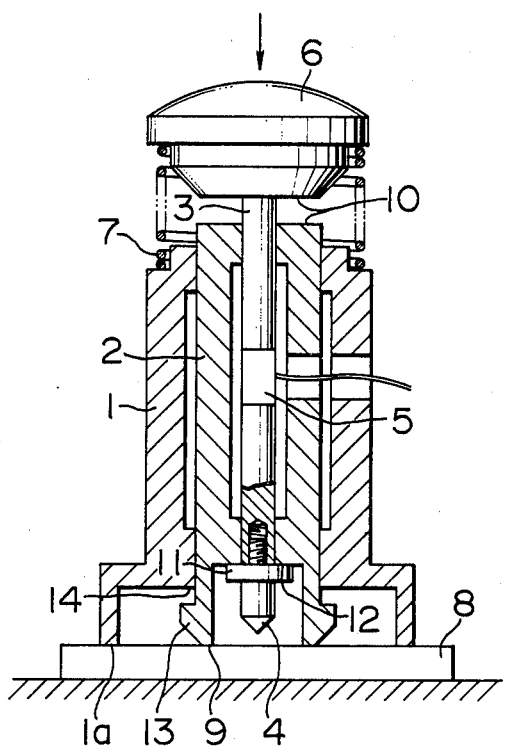
FIG. 1 is a vertical cross-sectional view of a hardness tester embodying this invention.

In FIG. 1, a reference cylinder 2 is coaxially and slidably fitted inside a guide cylinder 1. On the inside of the reference cylinder 2 is fitted, also coaxially and slidably, a load application shaft 3.

To the load application shaft 3 is fixed an indenter 4 at the lower end thereof, and a load detector 5, such as a load cell or stress-voltage transducer, in a higher position than the indenter 4.

A press member 6 is mounted on the top of the load application shaft 3, a spring 7 being interposed between the external periphery of the press member 6 and a shoulder portion of the guide cylinder 1.

A datum plane 9 that comes in contact with a specimen 8 is provided at the lower end of the reference cylinder 2. Also, a stop means or stopper mechanism 10 is provided by a top surface of a reference cylinder 2 and the bottom surface of the press member 6, these surfaces facing one another, for ultimate contact with one another as will be described presently, to regulate the axial movement of the load application shaft 3 relative to the reference cylinder 2.

The load application shaft 3 is normally pushed up by the spring 7, so that its lower flange 11 is in contact with a receiving surface 12 at the lower end of the reference cylinder 2. Accordingly, the reference cylinder 2 also is pushed up by the spring 7, thereby keeping its lower flange 13 in contact with a receiving surface 14 at the lower end of the guide cylinder 1. So, the datum plane 9 at the lower end of the reference cylinder 2 is normally held slightly above the bottom plane or surface 1a of the guide cylinder 1 although FIG. 1 shows these planes coinciding.

In measuring the hardness of the specimen 8, the guide cylinder 1 is first placed thereon, and then the press member 6 is pressed downward against the force of the spring 7 to lower the load application shaft 3. Therefore, the reference cylinder 2 carried on the lower flange 11 of the load application shaft 3 also descends until the datum plane 9 at the lower end thereof comes in contact with the upper surface of the specimen 8.

When the press member 6 is further depressed, the load application shaft 3 alone is lowered, and the indenter 4 at the lower end thereof contacts and, then, penetrates into the specimen 8. But since the penetrating amount of the indenter 4 into the specimen 8 is limited by the stopper mechanism 10, the indenter 4 is always permitted to penetrate therein only to a predetermined depth, making an indentation of a predetermined area, as explained above.

Namely, once the load application shaft 3 is pressed down through the press member 6 to the point where the stopper mechanism 10 functions, any additional load applied by further depression of the press member 6 is channelled through the stopper mechanism 10 to the reference cylinder 2, and thence through the datum plane 9 at the lower end thereof to an area on the specimen surrounding the indentation, and which does not affect the hardness measurement.

Because the stopper mechanism 10 is located above the load detector 5, the load detected thereby is that which has been used to penetrate the indenter 4 into the specimen 8.

By this means, hardness of the specimen 8 is simply determined as a function of the indenting force F measured by the load detector 5, it is unnecessary to make the precise measurement of the area or depth of indentation which, as mentioned, is required in the use of conventional hardness testers of the indenting type.

Figure 3:
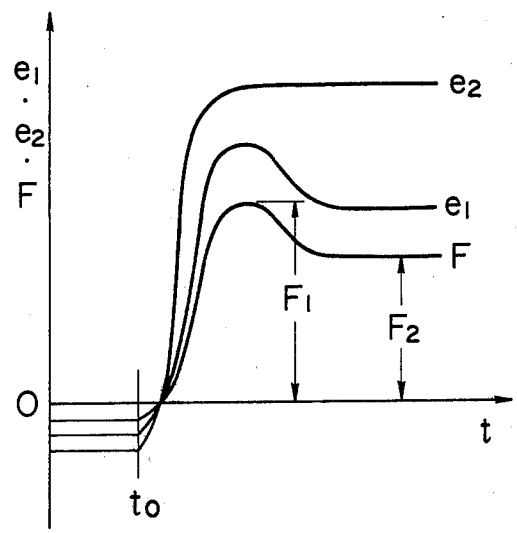
FIG. 3 is a graphical representation of the time-wise changes in outputs of these connected parts.

The maximum force detected by the load detector 5 is expressed as $F_1$, which is reached at the moment when the indenter 4 has penetrated into the specimen 8 to the predetermined extent that is controlled by the stopper mechanism 10. After that moment, the indenter 4 builds up a permanent strain in the specimen 8, and therefore the penetration of the indenter 4 is kept at the predetermined level by the force $F_2$, which is a little smaller than $F_1$ (FIG. 3).

With this hardness tester, hardness H is determined as a function of the maximum value $F_1$; that is, $H = f(F_1)$.

Figure 2:
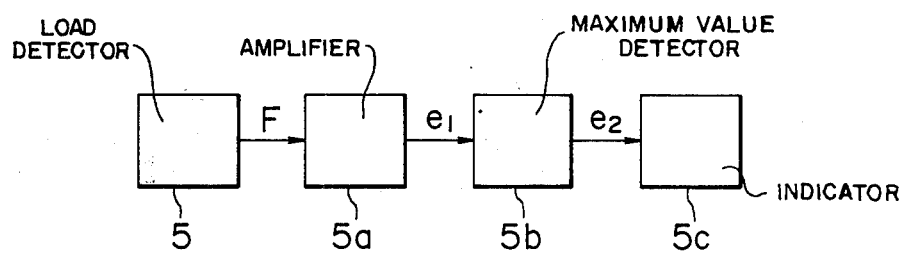
FIG. 2 is a block diagram showing the connected relationship between the load detector and the hardness indicator of the hardness tester in FIG. 1.

Accordingly, a maximum value detector 5b is connected through an amplifier 5a to the load detector 5, as illustrated in FIG. 2. Further, an indicator 5c to indicate the hardness determined from this maximum value is connected to the maximum value detector 5b.

The amplifier 5a, maximum value detector 5b and hardness indicator 5c are enclosed in a case not shown, and are attached to the press member 6.

FIG. 3 shows how the output F of the load detector 5, the output $e_1$ of the amplifier 5a, and the output $e_2$ of the maximum value detector 5b change with the lapse of time t during which hardness measurement is conducted. In this graph, $t_o$ indicates the point at which the indenter starts to penetrate into the specimen. Before the point $t_o$, the values of F, $e_1$ and $e_2$ are all negative, since the load detector 5 receives a tensile force under the influence of part of the weight of the load application shaft 3 and the weight of the reference cylinder 2.

Figure 4:
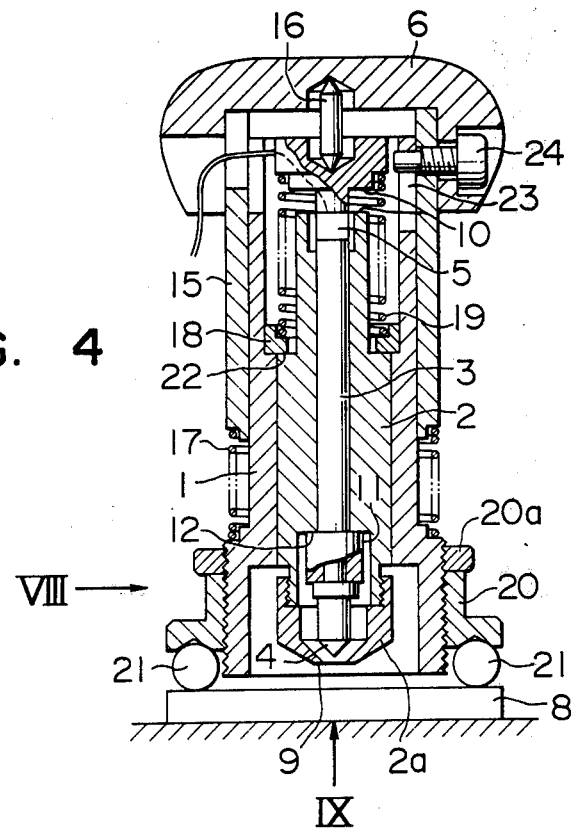
FIG. 4 is a vertical cross-sectional view of another hardness tester embodying this invention.

FIG. 4 is a vertical cross-sectional view of another hardness tester embodying this invention, in which similar reference numerals designate such parts as are similar to those in FIG. 1; that is, the reference cylinder 2 is coaxially and slidably fitted in the guide cylinder 1, the load application shaft 3 is coaxially and slidably fitted in the reference cylinder 2; the load application shaft 3 has the indenter 4 at the lower end thereof; and the load detector 5, such as a load cell, is disposed at the top thereof.

In this second embodiment, a press cylinder 15 is coaxially and slidably fitted outside the guide cylinder 1, and a pivot 16 to transmit the pressing load is provided between the press member 6, fixed to the top of said press cylinder 15, and the upper end of the load application shaft 3.

A spring 17 is interposed between the lower end of the press cylinder 15 and a lower step or shoulder of the guide cylinder 1, and another spring 19 between a spring shoe 18 in the guide cylinder 1 and an upper shoulder or step of the load application shaft 3.

To the lower end of the reference cylinder 2 is screwed a reference member 2a having the datum plane 9 that comes in contact with the specimen 8. By means of this reference member 2a, the position of the datum plane 9 of the reference cylinder 2 can be adjusted.

Also, a contact-bar holder 20 is screwed and fixed with a nut 20a to the lower end of the guide cylinder 1. Two round contact bars 21, which are to be placed on the specimen 8, are horizontally fixed in grooves formed in the bottom surface of the contact-bar holder.

The load application shaft 3 normally is pushed up by a spring 19 and, therefore, its lower flange 11 is in contact with the receiving surface 12 at the lower end of the reference cylinder 2. Consequently, the reference cylinder 2 is pushed up by the spring 19, shaft 3 and flange 11, whereby an intermediate step 22 of cylinder 2 is in contact with the lower end of the spring shoe 18. Therefore, the datum plane 9 is held above the lower surface of the contact bars 21, as shown.

In measuring the hardness of the specimen 8, the contact bars 21 are first placed on the specimen 8. By subsequently depressing the press member 6 against the force of the spring 17, the load application shaft 3 is lowered. Since the pressing load is transmitted through the pivot 16, no detrimental rotating torque is imparted to the load application shaft 3.

As the load application shaft 3 descends, the reference cylinder 2 having its lower surface 12 resting on flange 11, also goes down until its datum plane 9 comes in contact with the upper surface of the specimen 8.

When the press member 6 is further pressed down, the load application shaft 3 alone descends against the force of the spring 19. Ultimately, the indenter 4 at the lower end thereof contacts and, then, penetrates into the specimen 8. But the penetrating amount of the indenter 4 into the specimen 8 is controlled to a predetermined value by means of the stopper mechanism 10 consisting of the upper end of the reference cylinder 2 and, facing this end, a shoulder or protruding part at the upper end of the load application shaft 3.

Because the stopper mechanism 10 is located above the load detector 5, the load detected by the load detector 5 is that which has been used to penetrate the indenter 4 into the specimen 8. Thus, hardness of the specimen 8 is determined as the function of the force measured by the load detector 5, as in the case of the aforesaid first embodiment.

Figure 5:
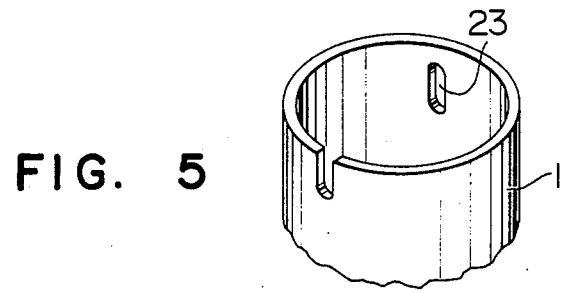
FIG. 5 is a perspective view of the upper part of the guide cylinder of the hardness tester of FIG. 4.

FIG. 5 shows the upper end of the guide cylinder 1, in which a vertically extending slot 23 is formed so that a bolt 24 screwed through the press cylinder 15 is received thereby as illustrated in FIG. 4. By this means, the press cylinder 15 is prevented from rotating, while it is permitted to move up and down, with reference to the guide cylinder 1.

Figure 6:
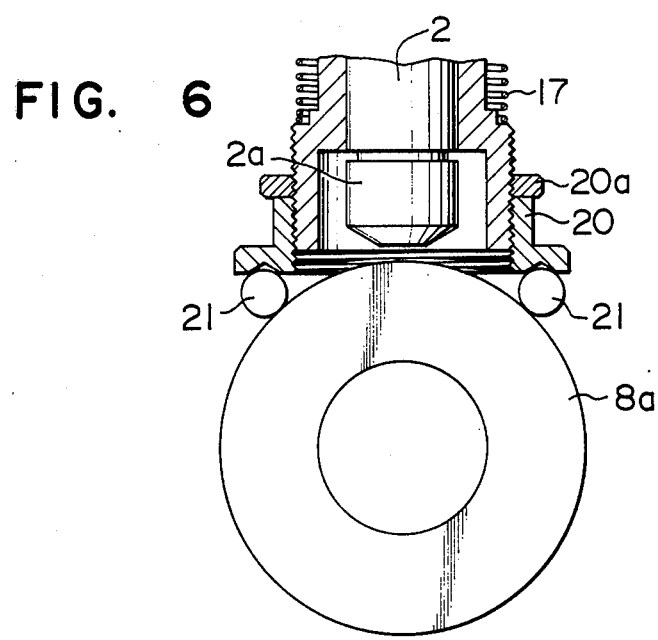
FIGS. 6 and 7 are partial cross-sectional views illustrating the hardness tester of FIG. 4 being used under different conditions.

FIG. 6 is a partial cross-section that shows a condition in which hardness of the external surface of a cylindrical specimen is being measured. By adjusting the position of the contact-bar holder 20 relative to the guide cylinder 1 by means of the nut 20a, the two contact bars 21 are brought into contact with the cylindrical specimen 8a, in parallel with the axis thereof. As a consequence, the hardness tester is mounted on the external surface of the cylindrical specimen 8a in such a manner as to insure stable measurement of hardness.

Figure 7:
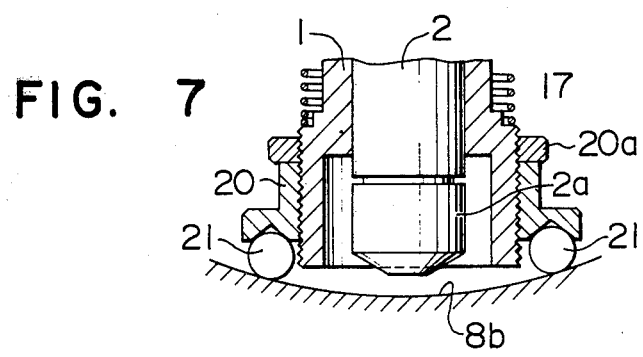

FIG. 7 is a partial cross-section showing a condition in which hardness of the internal surface of a cylindrical specimen is being measured. As in the case of FIG. 6, the contact bars 21 are placed on the cylindrical specimen 8b in parallel with its axis, thereby insuring stable hardness measurement.

Figure 8:
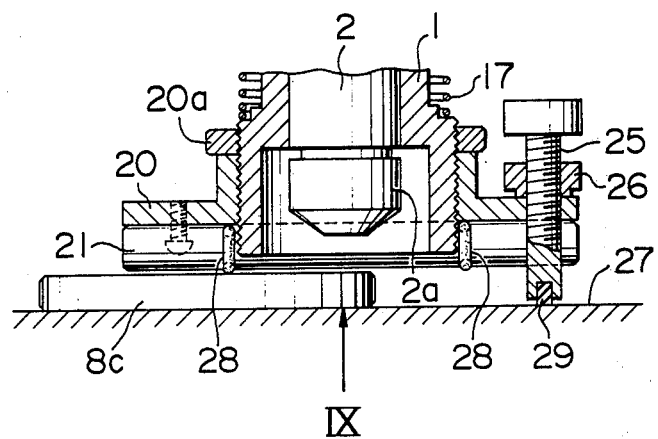
FIG. 8 is a cross-section looking in the direction of arrow VIII in FIG. 4.
Figure 9:
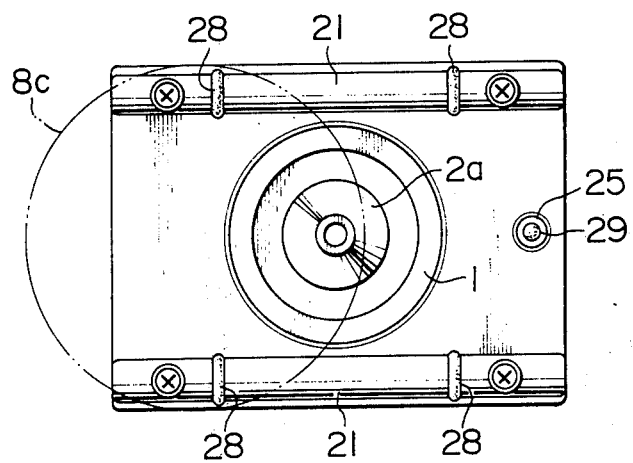
FIG. 9 is a view looking in the direction of arrow IX in FIGS. 4 and 8.

FIG. 8 is a cross-section looking in the direction of arrow VIII in FIG. 4, while FIG. 9 is a sectional plan view looking in the direction of arrow IX in FIGS. 4 and 8. As illustrated in these figures, a threaded bolt 25 screwed through the contact-bar holder 20 is fixed by a nut 26, whereby the level of the lower end of said bolt 25 is adjustable with reference to the contact bars 21.

On account of this arrangement, the hardness tester can be held in a stable manner, even when hardness of the edge portion of the specimen 8c is measured, by means of the two contact bars 21 placed thereon and the one threaded bolt 25 erected on an anvil 27.

Rubber rings 28 are fitted in grooves formed along the circumference of each contact bar 21, so that they come into frictional contact with the surface of the specimen, on being deformed and withdrawn into said grooves, when the guide cylinder 1 is pressed during hardness measurement.

Also, a rubber piece 29 is fitted in an opening formed at the lower end of the threaded bolt 25, so that it also becomes withdrawn into the opening and comes into frictional contact with the anvil 27, just as the rubber rings 28 do, when the guide cylinder 1 is depressed. By their frictional contact, the hardness tester can be held on the specimen more stably.

What is claimed is:
1. A hardness tester, comprising;
   a load application shaft having an indenter at a lower end thereof, and having loading means at an upper end thereof for applying variable loads to the shaft to press the indenter into a specimen;
   a reference cylinder coaxially fitted around the shaft for sliding of the shaft along the cylinder, the cylinder having a datum plane at a lower end thereof for contacting the specimen at the inception of the applying of a load to the shaft;
   stop means on the shaft and cylinder for limiting any sliding of the shaft, downwardly along the cylinder, to a predetermined length to limit the pressing of the indenter into the specimen to a predetermined corresponding depth;
   a load detector on the shaft between the indenter and the loading means for detecting loads applied to the shaft by the pressing of the indenter into the specimen; and
   means for indicating the load applied to the shaft and detected upon the pressing of the indenter into the specimen to the predetermined depth, to thereby indicate a corresponding hardness of the specimen without any need for measuring variable dimensions of an indentation.

2. A hardness tester according to claim 1, in which the load detector comprises a stress-voltage transducer.

3. A hardness tester according to claim 2, in which the means for indicating the load includes a maximum value detector to detect a maximum voltage provided by the transducer.

4. A hardness tester according to claim 1, also including a guide cylinder mounted coaxially around the reference cylinder for sliding movement of the reference cylinder along the guide cylinder, the guide cylinder having a surface at a lower end thereof for contact with a surface of the specimen to guide the reference cylinder and thereby the shaft normally of the surface of the specimen.

5. A hardness tester according to claim 4 also including a press cylinder mounted coaxially around the guide cylinder for sliding movement of the guide cylinder along the press cylinder; and spring means for controlling the relative sliding movements of the cylinders and shaft to facilitate the limiting of the pressing of the indenter into the specimen.

* * * * *